United States Patent [19]

Gleeson, III

[11] Patent Number: 4,902,274

[45] Date of Patent: Feb. 20, 1990

[54] MULTIPLE AFFERENT SENSORY STIMULATION DEVICE

[76] Inventor: William J. Gleeson, III, 2319 W. Rapallo Way, Tucson, Ariz. 85741

[21] Appl. No.: 255,480

[22] Filed: Oct. 11, 1988

[51] Int. Cl.⁴ .......................................... A61M 21/00
[52] U.S. Cl. .................................................. 600/27
[58] Field of Search ............... 84/464 R; 600/26, 27, 600/28

[56] References Cited

U.S. PATENT DOCUMENTS

| | | |
|---|---|---|
| 3,240,099 | 3/1966 | Irons . |
| 3,292,861 | 12/1966 | Kawamura . |
| 3,343,453 | 9/1967 | Butterfield . |
| 3,473,428 | 10/1969 | Phillips ............... 128/2.05 |
| 3,804,503 | 4/1974 | Sissom ................... 84/464 |
| 3,919,915 | 11/1975 | Isbell ..................... 84/484 |
| 3,958,113 | 5/1976 | Termohlen . |
| 4,097,917 | 6/1978 | McCaslin . |
| 4,117,265 | 9/1978 | Gerlach ............... 179/1 SP |
| 4,172,406 | 10/1979 | Martinez ............. 84/464 R |
| 4,622,881 | 11/1986 | Rand .................... 84/464 R |

FOREIGN PATENT DOCUMENTS

| | | | |
|---|---|---|---|
| 2426988 | 4/1976 | Fed. Rep. of Germany | .... 84/464 R |
| 3204704 | 8/1983 | Fed. Rep. of Germany | .... 84/464 R |
| 3309589 | 9/1984 | Fed. Rep. of Germany | .... 84/464 R |
| 2390050 | 1/1979 | France | ............... 84/464 R |
| 1122330 | 11/1984 | U.S.S.R. | ............. 84/464 R |

Primary Examiner—Lee S. Cohen
Assistant Examiner—Scott Getzow
Attorney, Agent, or Firm—J. Michael McClanahan

[57] ABSTRACT

An improved multiple afferent sensory stimulation device is provided to receive a prerecorded tape program upon which the audio stimulation and control signals for the visual stimulation of a subject person's eyes and ears is provided, the invention consisting of a reproducing device to emit the audio and visual control signals on separate channels, the audio stimulation proceeding to earphones worn by the subject person, and the visual stimulation control signals processed electronically. This electronic processing includes amplifiers receiving the electronic signals for amplification, means to convert the AC signals to stretched out positive pulses, and means to utilize the stretched pulses to turn on and turn off the visual stimulation components of the invention. Visual stimulation components utilized may be electrofluorescent lights or incandescent bulbs placed directly in front of the subject person's eyes. Various different schemes of audio and visual sensory stimulation are suggested for achieving a mental and physical affect upon the subject person.

14 Claims, 1 Drawing Sheet

MULTIPLE AFFERENT SENSORY STIMULATION DEVICE

BACKGROUND OF THE INVENTION

1. Field of the Invention

The field of the invention is devices which simultaneously provide visual and audio stimulus to a person wearing a set of earphones and goggles with light stimulus in the front of the goggles.

2. Description of Related Art

Researchers have discovered that through the use of visual and audio stimulus, certain reactions may be induced into a person such as relaxation, altered states of consciousness, and increase of the brain's functional intelligence. Such an application of stimuli to a subject person and the reaction obtained is termed "multiple afferent sensory stimulation" or MASS.

These effects are produced through different combinations of visual and audio stimulus at different frequencies and in different rhythms. A total of four separate stimuli are available for energizing, one for each eye and for each ear, and such energizing may take many varied forms. The visual stimulus, if considering only one single color entity, such as an incandescent lamp, may have its brightness continually increased or decreased, may take the form of pulsed brief flashes of light which in turn can vary in brightness, or may be patterns over time or brillance formed with the pulses of light. For example, the pulses could be evenly spaced and of the same time width for one lamp brightness, or the lamp brightness could be increasing or decreasing by changing the pulse duty cycle. Further, the visual stimulus for each eye need not be the same.

The mode of operation of the audio stimulus can have many of the characteristics of the visual stimulus, such as pulsed tone, although, and perhaps preferably, music or pink noise may be substituted for a tone or combination of tones. The volume of the audio sounds can be increasing or decreasing, can consist of chopped sounds which again may be increasing or decreasing in intensity, and the duty cycle may be changed, i.e., the portion of the time that a sound is present compared to one complete cycle of sound present and not present.

Again, each sound stimulus for each ear need not be the same either.

Machines varying the visual and audio stimulus discussed above have been developed in the prior art.

It is reported that the human brain has basic frequencies at which it operates and which have been observed by recording equipment such as an electroencephalograph (EEG). These so called "brain waves" generally fall into four classifications in accordance with their frequency rate, namely Beta, Alpha, Theta, and Delta. Beta waves occur during a person's awake time and occupies a frequency spectrum of between approximately 12 and 30 Hz. (cycles per second). Generally, the higher the frequency, the more intense the mental activity. Alpha waves occur during relaxation and during that twilight state just before sleep. Alpha waves occupy the frequency spectrum of approximately 8 to 12 Hz. Theta waves represents the frequency spectrum between 4 and 8 Hz and generally reflect brain activity during sleep or deep meditation. Lastly, Delta waves occur during times of deepest sleep and are generally in the range of 1 to 4 Hz.

It has been determined by researchers, such as Dr. George Corges, that a person's brain can be persuaded to operate in any of these four frequency spectrums by the application of visual and audio stimuli supplied in a desired frequency spectrum. The person's brain activity tends to "synchronize" with the frequency rate of the applied stimulus for certain defined stimulus.

By slaving the visual stimulus, such as repetitive blinking lights, with the audio stimulus, such as repetitive tones, a person will soon find their brain wave frequency, and thus mental activity, synchronizing to the applied visual or audio stimulus.

Obviously, various alternating modes of applied stimulus are possible by alternating between the left and right side eyes and ears in one or more of the sixteen possible combinations from no stimulus present on all four receptors (left and right eyes, left and right ears) to stimulus for all four receptors. In addition, the pattern of the stimulus can be varied as eluded to above.

Of course, some combinations of stimulus will result in less reaction of the person while other combinations of stimulus will result in a profound reaction.

Further, while it would be apparent that a scheme of application of structured visual and audio stimulus to a person would produce the best or desired reaction, yet it is possible to achieve desirable reactions by utilizing as the audio stimulus what is commonly termed "pink noise", which is a variation of "white noise". White noise is random electrical noise that exists in electronic circuits due to electron shot and thermal noise defined as having constant energy per unit band waves and independent of any central frequency of a band. The name is taken from the analogous definition of white light, which is the combination of light of all colors in the light spectrum. Pink noise is white noise having the special characteristics that its intensity is inversely proportional to its frequency over a specified range. In pink noise, equal power is dissipated into a constant resistance in any octave band width in that range. Pink noise when heard, can have a very soothing effect, much like the sounds of ocean surf.

All of the stimulus, both visual and audio, with its variations, can be pre-programmed upon magnetic tape and then, through properly designed equipment, be presented to a person to achieve the desired mental and physical effects.

Accordingly, it would be useful to have a device adapted to take information pre-recorded on such a medium as magnetic tape, to decipher it through electronic circuits, and deliver the resultant electronic signals to generators of visual and audio stimulation surrounding a subject person.

SUMMARY OF THE INVENTION

The invention relates to an improved multiple afferent sensory stimulation device receiving on prerecorded tape, a series of electronic signals which, after processing, control the placement of visual or sound stimulus before a subject person's eyes and ears.

In the preferred embodiment, one tape recorder with four playback heads is utilized with a prerecorded four channel tape. Upon two of the channels of the tape are recorded the audio signals such as pink noise or music which are to be heard by the subject, one channel for the left ear and a second channel for the right ear. One audio channel does not necessarily have the same recorded program as the other, although it may. The other two channels of the prerecorded tape contain the electrical control signals which regulate the visual stimulus presented to each of the subject's eyes, one channel for the left eye and one channel for the right eye.

In an alternate embodiment, two tape recorders with two separate prerecorded tapes are utilized, one tape recorder presenting the two audio channel outputs and the other tape recorder presenting the two electrical control signal outputs. If desired, the two tape recorders may be slaved to each other so that the audio portion is in synchronization with the visual stimulation control signals or, if pink noise is recorded on the two audio channels of the prerecorded tape, it may not be necessary or desirable to synchronize the prerecorded tapes. This would most likely be the situation for a relaxation mode where the sound of surf is to be played in the earphones while a relaxing pattern of visual stimulus is presented in accordance with control signals on the prerecorded tape.

The electronic circuitry which receives the electrical output of each channel of visual stimulation control signals from the tape recorder is identical to the other channel and, the electronic circuitry receiving the electrical output from the tape recorder for each audio channel connected to the left and right headsets is also identical.

The visual stimulation electrical control signals eminating from the first and second output channels on the tape recorder or playback device are first directed to a visual processing circuit means having firstly a buffer amplifier receiving the AC component of the signal after it has been DC isolated from the tape recorder and a fixed DC bias added at its entrance to the buffer operational amplifier input. The buffer amplifier is in a feedback mode to regulate gain in order that a sufficiently large signal is available for processing. The electrical control signals, as received from the tape recorder channels, nominally comprises 2 kHz sine wave bursts of signal upon each line.

The output of the buffer amplifier, normally 6 volts peak to peak, is directed to a second DC isolation capacitor and then the negative going portion of the signal below approximately zero volts DC is shunted to ground through a negative clamping diode. The positive going portions of the 2 kHz signal burst passes a forward biased rectifying diode which acts much like a half-wave rectifier to charge a capacitor in a pulse stretching circuit to form a positive pulse having a width equal to the total number of positive going sine wave portions in the 2 kHz burst of control signal. Amplitude of the resultant signal is approximately 5 volts relative to ground.

The control signal, now looking somewhat like the positive portion of a square wave or elongated pulse, is directed to the gate of a turn on-turn off field effect transistor which turns on hard upon receipt of the signal and stays on throughout the duration of the signal. The drain of the field effect transistor is then directed to the visual display circuit. In the event an incandescent light bulb is utilized, the 9 volt power source is directed through the light bulb and through the FET drain to its source and onto ground. If an electrofluorescent light is utilized, the 9 volt source is fed to one side of a DC/AC power inverter with the output of the power inverter directed to the field effect transistor drain with the FET's source grounded.

The visual stimulation means is placed in front of the subject person's eye, usually taking the form of being encapsulated in the eye lenses of a pair of goggles. When utilizing an incandescent bulb, the lenses of the goggles are opaque and may be termed blinders. The bulb is placed immediately inside each blinder in order that the subject person see nothing except light emitted from the bulb. In the case utilizing the electrofluorescent lights, the electrofluorescent lights are the blinders, and the output of the previously described DC/AC power inverter is directed to these blinders and application of voltage turns the electrofluorescent lights on. During the absence of the control signal, the electrofluorescent lights darken and the subject person sees the dark blinder, i.e., no light at all.

An audio circuit means consisting of an earphone receives the audio stimulation signals from the playback device's third and fourth outputs to supply the audio stimulation to the subject person.

It is an object of the subject invention to provide a device for processing signals from prerecorded tapes to provide multiple afferent sensory stimulation of the auditory and visual senses.

It is another object of the subject invention to provide a multiple afferent sensory device which processes auditory and visual stimuli for separate audio and visual stimulus.

It is another object of the subject invention to provide a multiple afferent device which receives encoded signals from prerecorded tapes so that the auditory and visual stimulation devices may be separately controlled.

Other objects of the invention will in part be obvious and will in part appear hereinafter. The invention accordingly comprises the apparatus comprising the construction, combination of elements, and arrangement of parts which are exemplified in the following detailed disclosure and the scope of the invention which will be indicated in the claims.

BRIEF DESCRIPTION OF THE DRAWINGS

For further understanding of the nature and objects of the subject invention, reference should be had to the following detailed description taken in connection with the accompanying drawings wherein.

In various views, like index numbers refer to like elements.

DETAILED DESCRIPTION OF THE PREFERRED EMBODIMENT

Figure 1:
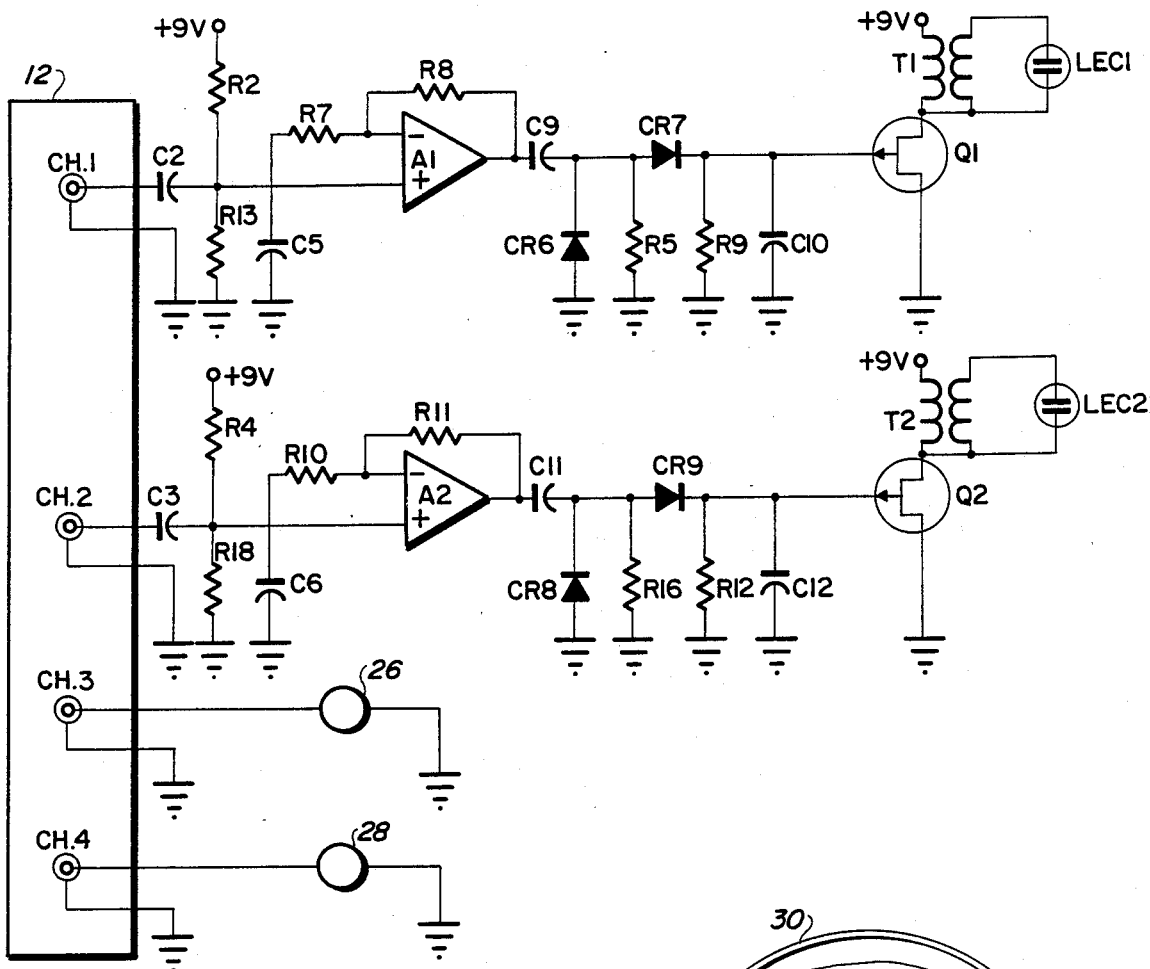
FIG. 1 is a schematic diagram of the subject invention.

Referring firstly to FIG. 1, a complete schematic diagram is shown of the invention which permits sensory stimulation of the visual and audio senses of a subject person, the stimulus in each of the subject person's ears or eyes capable of being provided separately or together in all conceivable combinations. For example, one ear could be stimulated with sound without stimulating the other ear or visually stimulating either of the left or right eyes. The possible combination from no stimulus to any stimulus receptor (eyes or ears) to all four receptors receiving stimulus is 16.

Further, the combinations of stimulation is further increased because the light stimulation can be in combination of different brightnesses, or its brightness may be varied, either becoming more bright, or going less bright. Similarly, the audio stimulation can be at any volume, from very soft to very loud, or like the visual stimuli, may be increasing in volume or may be decreasing in volume. Further, both the audio and the visual stimulus can be pulsed in innumerable combinations. It is apparent that there is practically an unlimited number of combinations in which the four sensory organs may be stimulated.

Such sensory stimulation is accomplished by the circuit shown in FIG. 1. Proceeding from the top left to right, at the far upper left is the playback device 12 such as a magnetic tape playback recorder or other machine which utilizes a prerecorded four channel tape with encoded data on two channels and audio on two channels, the visual stimulation control electrical signals emitted on the first two channel outputs, a left or first channel output 1 and a right or second channel output 2 and the audio stimulation signals emitted on the second two channel outputs, namely left or third channel output 3 and right or fourth channel output 4. The tape has been pre-programmed with the desired visual control signals, comprising a 2 kHz sine wave which may consist of bursts of signal which in itself may be repeating, such as at a 10 cycle rate, or the 2 kHz sine wave may be continuous for relatively long periods of time.

Any DC component on the output electrical control signal of channel 1 of playback recorder 12 is directed to the visual processing circuit means and firstly isolates the inventive circuit by first DC isolation capacitor C2 and thus only the AC component of the signal is passed. Thereafter, the output signal of channel 1 is dc biased by means of connection to the common point of a voltage divider network made up of resistors R2 and R13, the other end of resistor R2 attached to the source of DC power with the other end of resistor R13 grounded. The AC signal received from channel 1, now raised above zero volts by its fixed DC bias, an amount of approximately a positive 4.5 volts, is fed into the positive input of buffer operational amplifier A1. Buffer amplifier A1 is connected in a feedback mode with its gain set by the ratio of resistor R8 over R7. A gain of about 10 is desired. Further, the negative input to buffer amplifier A1 is also grounded through resistor R7 and capacitor C5 which provides a DC reference voltage of about 4.5 volts.

The output of buffer amplifier A1 consists of a 2 kHz sine wave having an amplitude of about 6 volts peak-to-peak. The output signal is then DC isolated from the remainder of the circuitry by in-line second DC isolation capacitor C9. Resistor R5 connected to capacitor C9 is grounded and provides an essentially constant load to the output of buffer amplifier A1 in order that the voltage at the junction of capacitor C9 and resistor R5 will approach ground when no input signal is present at the input to buffer amplifier A1. The signal is negatively clipped by reverse biased negative grounding diode CR6 which grounds all negative portions of the signal greater than the drop across the diode, nominally 0.6 volts or so.

Continuing, the output signal from channel 1, which is now substantially all positive going and consisting of the positive wave forms of the sine wave, now passes through forward biased rectifying diode CR7 (acting like a half-wave rectifier) to the pulse stretching circuit to charge capacitor C10, one lead of capacitor C10 being grounded. At this point, the gap or space between the positive going portions of the sine wave are filled in by the charge stored previously on capacitor C10, which charge is also slowly being continuously drained by bleed resistor R9 to ground. The net effect is that the signal at this point has been changed from a sine wave to a positive going elongated pulse having a width as wide as the number of sine wave cycles contained in the burst of the two kHz electrical control signal. When the control signal amplitude goes to zero, capacitor C10 will then start to drain through resistor R9 to form the falling or trailing edge of the positive going pulse.

The signal at this point is fed to the gate of Q1, a turn off-turn on field effect transistor (FET), to control the current through the transistor. The FET is a very high input impedance device and accordingly draws extremely little gate current from the signal. Upon Q1 being triggered, it closes the circuit between its drain and its source, the source being grounded. The drain of the FET is operably connected to the positive DC voltage which is the power supply voltage for the invention, nominally 9 volts DC.

In the visual display circuit means, when the visual stimulus control signals are to operate electrofluorescent lights placed immediately in front the subject person's eyes working as blinders in a pair of goggles, power inverter T1 is utilized with the electrofluorescent lights. In the embodiment shown in FIG. 1, the input voltage to power inverter T1 is connected between the drain of the transistor Q1 and the DC power supply, nominally 9 volts.

The electrofluorescent light is shown by the circle and nomenclature LEC1 in FIG. 1 and is caused to fluoresce by an AC current of nominally 110 volts. Accordingly then, power inverter T1, which is a commercially packaged unit, is a DC to AC power convertor stepping up 9 volt DC to 110 volt AC at a frequency of 400 hKz. For a continuously operating electrofluorescent light, an alternating current, preferably at 400 hz, is supplied by power inverter T1. To provide such a source of continuous alternating current from T1, the burst of 2 kHz cycle programmed on the prerecorded tape and appearing on channel 1 would need be continuous. Then, when it is desired in the operation of the device that the electrofluorescent light LEC1 should not fluoresce, the control signal is absent from channel 1. Obviously, pulsing of electrofluorescent light LEC1 is accomplished by pulsing bursts of electrical control signals.

The components and connecting of circuitry shown in FIG. 1 which receive the electrical control signal from channel 2 of playback device 12 is identical to channel 1 and the circuitry similarly operates. Accordingly, discussion of this circuit would be the same as the above discussion of the circuit receiving the signal from channel 1 and for that reason is omitted.

Figure 2:
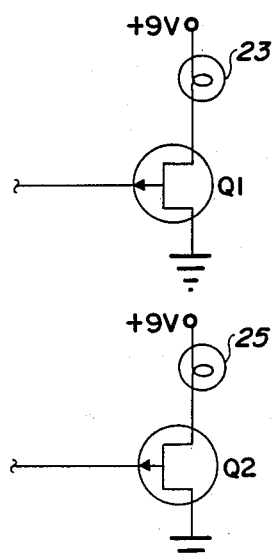
FIG. 2 is a partial schematic diagram of an alternate embodiment of the subject invention.

An alternate embodiment of the invention is shown in FIG. 2 where the power inverters T1 and T2 and the electrofluorescent lights LEC1 and LEC2 of the visual display circuit means have been removed and incandescent bulbs or lights 23 and 25 respectively substituted. So long as current is flowing through the field effect transistors Q1 and Q2, incandescent bulbs 23 and 25 will light. Alternately, pulsed signals may power bulbs 23 and 25 if desired. Further, brightness or dimness of the bulb may be controlled by pulsed electrical control signals having a repitition rate above the eye's discerning level but having a duty cycle such that the amount of time that current is flowing through the filament of the bulb is varied to achieve the desired resultant effect.

The balance of the schematic in FIG. 1 not previously discussed concerns the audio stimulation signals outputted from playback device 12, namely through output channels 3 and 4. These channels output audio sounds pre-programmed upon the third and fourth channels of the prerecorded tape to the audio circuit means consisting of a left and right headset earphone worn by the subject person. In FIG. 1, the output from channel 3 is directed to the left earphone 26, and the output of channel 4 from playback device 12 is directed to the right earphone 28.

Figure 3:
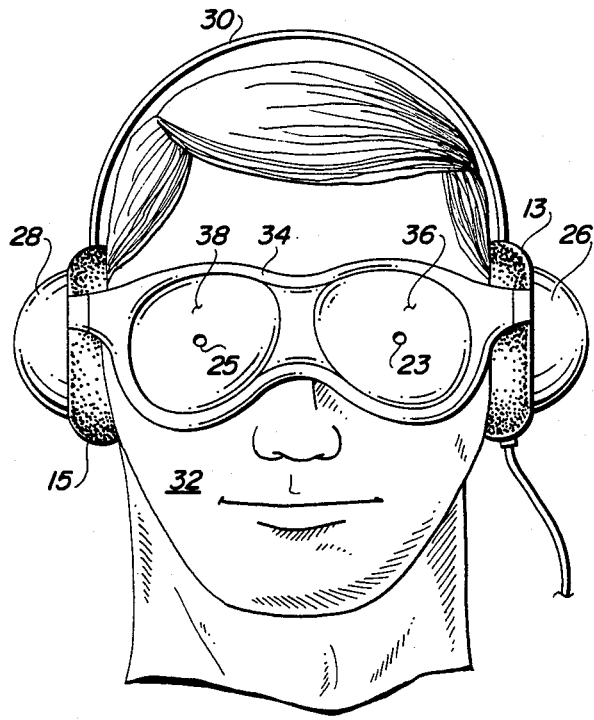
FIG. 3 is a front view of a subject person wearing the earphones and goggles receiving the audio and the visual stimuli.

Referring now to FIG. 3, a front view of a subject person utilizing the apparatus of the invention is detailed. Firstly, left and right earphones 26 and 28 respectively of headset 30 are shown mounted upon the head of the subject person 32. The headset is preferably spring loaded in the band connected to the two earphones so as to hold each earphone to the ear, each earphone utilizing elastic cushions 13 and 15 situated between the earphone and the ear so as to provide comfort to the subject person and to keep out extraneous sounds from interfering with the programmed audio sounds heard by the subject person 32. Situated proximate each of the subject person's eyes are a pair of goggles 34 which contain individual opaque blinders, left opaque blinder 36 and right opaque blinder 38, each separated from the other and light protected in order that no outside light enter the subject person's eyes.

In the preferred embodiment, left opaque blinder 36 and right opaque blinder 38 comprise the electrofluorescent lights LEC1 and LEC2 respectively. These lights, which are shaped as lenses for placement in a pair of goggles, are dark when not being excited by an AC electrical signal. In the alternative, opaque blinders 36 and 38 may have attached to them bulbs 23 and 25 respecitvely wherein the portion of the bulb containing the filament protrudes through the opaque blinders so that the light emitted from the bulb may be seen by the subject person. The bulbs are light sealed around the blinders.

Thus, the subject person 32 shown in the diagram of FIG. 3 has two inputs of audio stimulation and two inputs of visual stimulation, each separated from the other and each capable of being separately energized with an appropriate sound or control signal.

Since, as mentioned above, the visual stimuli presented can be either a very soft, dim light, or a very bright light, or a light increasing in brightness or a light decreasing in brightness, together with the light on or off with respect to real time, i.e., a series of light pulses over time in a coded group of light pulses, or as a continuous light, the visual stimulation obtained is an average of the actual number of pulses present to energize the light. A series of closely spaced pulses having a repetition greater than 60 Hz powering a lamp, for example, would appear to the subject person as a light constantly on. Similarly, if the on pulses are initially widely separated and then become closer spaced and are at a repetition rate greater than 60 Hz, the light will appear to a subject person as increasing in brightness. Certainly the inverse is true, from pulses which are closely spaced to pulses which are spaced further apart with respect to time will cause the light to appear to have reduced its intensity over a period of time. If the light utilized is an incandescent bulb, it will take some period of time before the blub emits light from the time that the electrical pulse is received as the filament must heat up to the point of becoming incandescent. Plus, in the case of incandescent lights, the filament tends to stay hot and emit light for a period after the pulse has passed. Thus, the incandescent bulbs may be made to have its light energy waning, or increasing, or pulsing, when all that is happening is the spacing of strings of electrical pulses.

Further, it is obvious that light emitting diodes (LED's) may be used in place of incandescent bulbs or electrofluorescent lights with modifications of the electronic circuitry all within the current state of the art.

Obviously then, a pulse width modulation can be used as the procedure for producing the visual stimuli control pulses.

In the preferred embodiment, the elements described in FIG. 1 comprise the following commercially available electronic circuits: amplifiers A1 and A2 are National Semiconductor LM741; transistors Q1 and Q2 are field effect transistors VN0610L manufactured by Siliconix, all diodes are 1N3600, and left and right electrofluorescent lights LEC1 and LEC2 are electroluminescent lights 0434 manufactured by Loctite Luminescent Systems, Inc. Lastly, power inverters T1 and T2 are Model No. BKL09-3-1 manufactured by ERG Inc.

TABLE I.

| Resistors Ohms | | Capacitors uf | |
|---|---|---|---|
| R2 | 100k | C2 | 10 |
| R4 | 100k | C3 | 10 |
| R5 | 3k | C5 | 10 |
| R7 | 10k | C6 | 10 |
| R8 | 100k | C9 | 1 |
| R9 | 5k | C10 | 10 |
| R10 | 10k | C11 | 1 |
| R11 | 100k | C12 | 10 |
| R12 | 5k | | |
| R13 | 100k | | |
| R16 | 3k | | |
| R18 | 100k | | |

While a preferred embodiment and three alternate embodiments have been shown and described, it will be understood that there is no intent to limit the invention by such disclosure, but rather it is intended to cover all modifications and alternate constructions falling within the spirit and the scope of the invention as defined in the appended claims.

I claim:

1. A multiple afferent sensory stimulation device providing audio and visual sensory stimulation to a subject person's ears and eyes to induce sensory reactions in the subject person comprising:

a play back device adapted to receive a prerecorded program and to emit visual stimulation control signals having an AC component from a first and second output and to emit audio stimulation signals from a third and fourth output;

visual processing circuit means operably connected to said playback device first output to receive the visual stimulation control signals, said visual processing circuit means including an operational amplifier having an input and an output, said operational amplifier input operably connected to said playback device first output to amplifier the visual stimulation control signals, and a pulse stretching circuit operably attached to said operational amplifier output to stretch the amplified visual stimulation control signals;

audio circuit means operably connected to said playback device third output to receive the audio stimulation signals and to provide audio stimulation to at least one of the subject person's ears; and visual display circuit means to display visual stimulation to at least one of the subject person's eyes, said visual display circuit means operably connected to said visual processing circuit means receiving the amplified and stretched visual stimulation control signals whereby audio and visual stimulation is provided to a subject person in accordance with the prerecorded program to induce sensory reactions into the subject person.

2. The multiple afferent sensory stimulation device as defined in claim 1 wherein said visual processing circuit means further includes a first DC isolation capacitor and voltage divider circuit, said DC isolation capacitor and voltage divider circuit operably connected between said playback device first output and said operational amplifier, said DC isolation capacitor passing the AC component of the visual stimulation control signals to said operational amplifier input and said voltage divider circuit providing a fixed DC bias to said operational amplifier input.

3. The multiple afferent sensory stimulation device as defined in claim 2 wherein said visual processing circuit means further includes a second DC isolation capacitor connected to the output of said operational amplifier, a negative grounding diode operably connected to said second DC isolation capacitor, and a rectifying diode also operably connected to said second DC isolation capacitor and said negative grounding diode, said rectifying diode also connected to said pulse stretching circuit.

4. The multiple afferent sensory stimulation device as defined in claim 3 wherein said visual processing circuit means further includes a turn on-turn off field effect transistor, said field effect transistor operably connected to said pulse stretching circuit.

5. The multiple afferent sensory stimulation device as defined in claim 4 wherein said audio circuit means includes an earphone operably attached to said playback device whereby audio stimulation is provided to the subject person 6. The multiple afferent sensory stimulation device as defined in claim 5 wherein said visual display circuit means includes a power inverter and an electrofluorescent light, said power inverter operably connected to said turn on-turn off field effect transistor, and said electrofluorescent light operably connected to said power inverter whereby when a signal is emitted from said playback device first output in accordance with a prerecorded program, the AC component of the signal passes the first DC isolation capacitor and then is DC biased for entry into the operational amplifier input, the amplified AC component of the signal then passing the second DC isolation capacitor whereupon the negative portion of the signal is grounded and the positive portion passed through the rectifying diode with the signal then stretched between adjacent positive portions to form an elongated pulse which turns on the field effect transistor to activate the power inverter and cause the electrofluorescent light to fluoresce and thus provide the visual stimulation to the subject person.

7. The multiple afferent sensory stimulation device as defined in claim 6 wherein said visual display circuit means includes an incandescent light operably connected to said turn on-turn off field effect transistor whereby when a signal is emitted from said playback device first output in accordance with the prerecorded program, the AC component of the signal passes the first Dc isolation capacitor and then is DC biased for entry into the operational amplifier input, the amplified AC component of the signal then passing the second DC isolation capacitor whereupon the negative portion of the signal is grounded and the positive portion passed through the rectifying diode with the signal then stretched between adjacent positive portions to form an elongated pulse which turns on the field effect transistor to permit current to flow through the incandescent light to cause it to illuminate and thus provide visual stimulation to the subject person.

8. A multiple afferent sensory stimulation device providing audio and visual sensory stimulation to a subject person's ears and eyes to induce sensory reaction in the subject person comprising:

a playback device adapted to receive a prerecorded program and to emit visual stimulation control signals having an AC component from a first and second output and to emit audio stimulation signals from a third and fourth output;

first and second visual processing circuit means operably connected to said playback device first and second output respectively to receive the visual stimulation control signals, each said first and second visual processing circuit means including an operational amplifier having an input and an output, said operational amplifiers inputs operably connected to said playback device first and second output respectively to amplify the visual stimulation control signals, and a pulse stretching circuit operably connected to each of said operational amplifiers outputs to stretch the amplifier visual stimulation control signals;

first and second audio circuit means operably connected to said playback device third and fourth output respectively to receive the audio stimulation signals and to provide audio stimulation to both of the subject person's ears; and first and second visual display circuit means to display visual stimulation to both of the subject person's eyes, said first and said second visual display circuit means operably connected to said first and said second visual processing circuit means respectively whereby audio and visual stimulation is provided to a subject person in accordance with the prerecorded program to induce sensory reactions in the subject person.

9. The multiple afferent sensor stimulation device as defined in claim 8 wherein each said first and second visual processing circuit means further includes a first DC isolation capacitor and voltage divider circuit, said DC isolation capacitor and said voltage divider circuit operably connected between said playback device first output and second output respectively and said operational amplifier, said DC isolation capacitor passing the AC component of the visual stimulation control signals to said operational amplifier input and said voltage divider circuit providing a fixed DC bias to said operational amplifier input.

10. The multiple afferent sensory stimulation device as defined in claim 9 wherein each said first and second visual processing circuit means further includes a second DC isolation capacitor connected to the output of said operational amplifier, a negative grounding diode operably connected to said second DC isolation capacitor, and a rectifying diode also operably connected to said second DC isolation capacitor and said negative grounding diode, said rectifying diode also connected to said pulse stretching circuit.

11. The multiple afferent sensory stimulation device as defined in claim 10 wherein each said first and second visual processing circuit means further includes a turn on-turn off field effect transistor, said field effect transistor operably connected to said pulse stretching circuit.

12. The multiple afferent sensory stimulation device as defined in claim 11 wherein each said first and second audio circuit means each include an earphone operably attached to said playback device whereby audio stimulation is provided to both the subject person's ears.

13. The multiple afferent sensory stimulation device as defined in claim 12 wherein each said first and second visual display circuit means includes a power inverter and an electrofluorescent light, said power inverter operably connected to said turn on-turn off field effect transistor, and said electrofluorescent light operably connected to said power inverter whereby when a signal is emitted from said playback device first and second output in accordance with the prerecorded program, the AC component of the signal passes the first DC isolation capacitor and then is DC biased for entry into the operational amplifier input, the amplified AC component of the signal then passing the second DC isolation capacitor whereupon the negative portion of the signal is grounded and the positive portion passed through the rectifying diode with the signal then stretched between adjacent positive portions to form an elongated pulse which turns on the field effect transistor to activate the power inverter and cause the electrofluorescent lights to fluoresce and thus provide the visual stimulation to the subject person.

14. The multiple afferent sensory stimulation device as defined in claim 12 wherein each said first and second visual display circuit means includes an incandescent light operably connected to said turn on-turn off field effect transistor whereby when a signal is emitted from said playback device first and second output in accordance with a prerecorded program, the AC component of the signal passes the first DC isolation capacitor and then is DC biased for entry into the operational amplifier input, the amplified AC component of the signal then passing the second DC isolation capacitor whereupon the negative portion of the signal is grounded and the positive portion passed through the rectifying diode with the signal then stretched between adjacent positive portions to form an elongated pulse which turns on the field effect transistor to permit current to flow through the incandescent lights to cause them to illuminate and thus provide visual stimulation to the subject person.

* * * * *